United States Patent
Horzewski (10) Patent No.: US 11,351,321 B2
(45) Date of Patent: Jun. 7, 2022

(54) DELIVERY TUBE AND METHODS FOR TRANSPORTING PARTICLES INTO THE RESPIRATORY SYSTEM

(71) Applicant: Qool Therapeutics, Inc., Mountain View, CA (US)

(72) Inventor: Michael J. Horzewski, San Jose, CA (US)

(73) Assignee: Pagonia Medical, Inc., Menlo Park, CA (US)

( * ) Notice: Subject to any disclaimer, the term of this patent is extended or adjusted under 35 U.S.C. 154(b) by 359 days.

(21) Appl. No.: 16/666,924

(22) Filed: Oct. 29, 2019

(65) Prior Publication Data

US 2020/0129716 A1    Apr. 30, 2020

Related U.S. Application Data

(60) Provisional application No. 62/752,920, filed on Oct. 30, 2018.

(51) Int. Cl.
*A61M 16/04* (2006.01)
*A61B 1/267* (2006.01)

(52) U.S. Cl.
CPC ....... *A61M 16/0402* (2014.02); *A61B 1/2676* (2013.01); *A61M 16/0434* (2013.01); *A61M 16/0486* (2014.02); *A61M 2205/3368* (2013.01)

(58) Field of Classification Search
CPC .......... A61M 16/0445; A61M 16/0447; A61M 16/0477; A61M 16/0479; A61M 16/0488;
(Continued)

(56) References Cited

U.S. PATENT DOCUMENTS

| 6,589,271 B1 | 7/2003 | Tzeng et al. |
| 6,729,334 B1 * | 5/2004 | Baran ................ B67D 7/06 |
| | | 128/207.14 |

(Continued)

FOREIGN PATENT DOCUMENTS

| WO | WO-2015038870 A1 | 3/2015 |
| WO | WO-2016138045 A1 | 9/2016 |

(Continued)

OTHER PUBLICATIONS

International Search Report and Written Opinion for PCT/US2019/058643 dated Jan. 15, 2020.

*Primary Examiner* — LaToya M Louis
(74) *Attorney, Agent, or Firm* — Wilson Sonsini Goodrich & Rosati (57) ABSTRACT

Apparatus for transporting particles through a patient's trachea into the respiratory system include a delivery tube having at least a ventilation lumen and a particle delivery lumen. The delivery tube has a centering device near its distal tip, such as a balloon eccentrically mounted on the tube to position an outlet of the particle delivery lumen near a centerline of the trachea above the carina branching into the right and left bronchus. A proximal end of the delivery tube connects to a source of particles, and a controller may be provided to adjust a rate and/or an amount of the particles delivered to the patient. In a specific example, frozen particles are delivered to control core body temperature. In other instances, the particle may be a medicament or other substance for effecting other therapies or diagnostic procedures.

15 Claims, 8 Drawing Sheets

(58) Field of Classification Search
CPC .......... A61M 16/0493; A61M 16/0495; A61M 16/0497
See application file for complete search history.

(56) References Cited

U.S. PATENT DOCUMENTS

| | | |
|---|---|---|
| 8,074,649 B2 | 12/2011 | Dhuper et al. |
| 8,100,123 B2 | 1/2012 | Belson |
| 2012/0167878 A1 | 7/2012 | Belson et al. |
| 2016/0346493 A1* | 12/2016 | Wight ................ A61M 16/0445 |
| 2019/0059708 A1* | 2/2019 | Lei .................... A61M 16/0463 |
| 2019/0254699 A1* | 8/2019 | Forde ................. A61B 17/3415 |

FOREIGN PATENT DOCUMENTS

| | | |
|---|---|---|
| WO | WO-2017072812 A1 | 5/2017 |
| WO | WO-2017132609 A1 | 8/2017 |
| WO | WO-2018111778 A1 | 6/2018 |

\* cited by examiner

DELIVERY TUBE AND METHODS FOR TRANSPORTING PARTICLES INTO THE RESPIRATORY SYSTEM

CROSS-REFERENCE TO RELATED APPLICATIONS

This application claims the benefit of Provisional No. 62/752,920, filed Oct. 30, 2018, the entire content of which is incorporated herein.

BACKGROUND OF THE INVENTION

1. Field of the Invention

The present invention relates generally to medical systems and methods. More particularly, the present invention relates to systems and methods for delivering particles, such as medicaments and frozen particles, to a patient's respiratory tract. The systems and methods find use in inducing hypothermia, drug delivery, ventilation, and bronchoscopy.

Methods and systems for effecting systemic hypothermia and optionally administering drugs by delivering ice, other frozen particles, or drugs to the lungs, abdominal cavity, and other target sites of a patient have been described and implemented by Qool Therapeutics, Inc., assignee of the present application. For example, WO/2016/138045 teaches that frozen saline particles (FSP) and other frozen particles can be delivered as an aerosol or as a series of boluses to a patient through a patient interface, such as an endotracheal tube. Other patents and patent applications assigned to Qool Therapeutics, Inc. further teach that drugs, biologicals, and other active agents, can be delivered to the lungs concurrently with (or independently of) FSP delivery. See, for example, US20120167878; U.S. Pat. No. 8,100,123; WO/2017/132609; and WO2018/111778.

While the systems and methods described in these patents and published applications are effective, there remains a need for improved and alternative FSP delivery tubes which deliver the FSP and/or drugs into a patient's lungs in an optimum fashion. In particular, it would be desirable to provide improved FSP delivery tubes which deliver the FSP in a manner that optimizes the distribution of FSP within the lungs while ensuring proper ventilation. It would be further desirable to provide designs which optimizes the relative position of the FSP within the trachea or bronchus as it is released from the delivery tube. It would be still further desirable to provide designs which can achieve optimum placement and alignment of the delivery tube's FSP exit port and delivery lumen within the trachea or bronchus with high repeatability and minimum effort. It would be still further desirable to provide delivery tubes which are atraumatic and minimize the risk of injury to the trachea or bronchus as they are advanced. At least some of these objectives will be met by the inventions described and claimed below.

2. Listing of the Background Art

Various tubes and masks for delivering FSP to a patient's lungs are described in commonly owned US U.S. Pat. No. 8,100,123 and published PCT applications WO/2016/138045; US20120167878; WO/2017/132609; and WO2018/111778, the full disclosures of which are incorporate herein by reference.

SUMMARY OF THE INVENTION

In a first aspect, the present invention provides a particle delivery tube suitable for delivering a variety of particles, powders and other dispersible materials. The particle delivery tubes of the present invention are suitable for delivering a variety of solid particles (SP) for therapeutic, diagnostic or other purposes to a patient's respiratory system including the trachea and the lungs. While certain disclosed embodiments are particularly suited for delivering frozen saline particles (FSP) intended for inducing systemic and/or localized hypothermia in a patient, FSP and other SP may also use in delivering medicaments, including small molecule drugs, large molecule drugs, biologics, stem cells, and other medicaments, materials, and substances, either alone or in combination. As used hereinafter and in the claims, a solid particle (SP) is intended to refer generally to any dispersible particulate material that can be delivered by the particle delivery tubes of the present invention, including but not limited to frozen saline particles (FSP).

The particle delivery tube comprises a tracheal tube having a distal tip, a proximal end, a ventilation lumen (for delivering a breathing gas to the patient) and a solid particle (SP) lumen for delivering SP to the patient's respiratory system. A proximal hub is connected in the proximal region of the tracheal tube, and a centering cuff having a centerline is positioned about or circumscribes an exterior surface of the distal end of the tracheal tube. The SP lumen extends along one side of the tracheal tube and is typically nested, arranged as a circular lumen nested in a crescent-shaped lumen, adjacent D-shaped lumens, or otherwise positioned within the ventilation lumen, where the ventilation lumen typically has a larger cross-sectional are than the SP lumen. The centering cuff is eccentrically positioned about the exterior surface of the tracheal tube so that a centerline of the centering cuff is aligned with the centerline of the SP lumen when the centering cuff is inflated. In this way, when the tracheal tube is positioned within a trachea or bronchus of the lungs, the centerline of the SP lumen will be aligned with the centerline of the trachea or bronchus, which alignment optimizes release of the SP into the trachea and lungs. In particular, by centering an exit port of the SP lumen along the centerline of the trachea, impingement of the SP against a wall of the trachea, carina, and bronchus is minimized (reducing the risk of trauma to the wall of the trachea, carina, and bronchus) and delivery and distribution of SP may be optimized, such as enhancing penetration of the SP deep into the lung if so desired.

In specific embodiments of the frozen particle delivery tube of the present invention, the ventilation lumen has a crescent-shaped cross section which defines a partially cylindrical channel along one side thereof. The SP lumen may be formed or "nested" within at least a portion of the partially cylindrical channel in order to maximize the area available for both the SP lumen and the ventilation lumen. In further specific examples, the tracheal tube comprises a multi-lumen extruded tubular body, usually including a cuff inflation lumen and an auxiliary lumen in addition to the ventilation lumen and the SP lumen. Other lumens may also be provided for other purposes.

In still further specific instances, the distal tip of the frozen particle delivery tubes will be beveled, typically at an angle in the range from 20° to 60°, more typically from 35° to 55°, and still more typically from 35° to 40°, usually being about 38°, relative to a longitudinal axis of the tracheal tube. Such beveling defines a leading edge and a trailing edge at the distal tip or end of the tracheal tube. In particular embodiments, the SP lumen has a distal outlet port near of the trailing edge of the distal tip of the tracheal tube and the ventilation lumen has a distal port extending to the leading edge of the distal tip of the tracheal tube. Such designs promote release of the SP into the ventilation gas as the gas is being released from the tracheal tube into the patient's lungs. In other instances, the ventilation lumen may have a distal port proximate the trailing edge of the distal tip of the tracheal tube, and the SP lumen may extend to the leading edge of the distal tip of the tracheal tube. The latter design can be configured to provide an ejection angle of the SP into the ventilation gas stream as the gas stream enters the trachea. In either embodiment, the eccentric centering cuff will be oriented to locate a centerline of the SP lumen along the centerline of the frozen particle delivery tube with inflated cuff so that the SP are released along the centerline of the trachea or bronchus in which the tracheal tube is deployed.

In other specific examples, the tracheal tube of the frozen particle delivery tube will be curved along its length in a manner similar to conventional endotracheal tubes. In still further examples, the hub of the frozen particle delivery tube will have or provide access to both an SP lumen and a ventilation lumen. The SP lumen of the hub will be aligned with the SP lumen in the tracheal tube, typically being aligned co-linearly along a generally straight line (with respect to the local anatomy's centerline) at a junction where the hub meets the tracheal tube. The ventilation lumen on the hub, in contrast, will typically be aligned at an angle relative to an axis of the ventilation lumen and the tracheal tube where they meet. In still further examples, the hub may be a bifurcation with extending tubes providing an SP lumen and a ventilation lumen, each extending tube with its own appropriate SP or ventilator fitting. In still further examples, the hub may be connected in a detachable manner to the tracheal tube. That is the hub may be removable from the tracheal tube to allow the user to shorten the length of the tracheal tube and then reconnect the hub to the tracheal tube for use.

In a second aspect, the present invention provides methods for lowering a core body temperature of a patient. The methods comprise providing a source of SP, typically frozen saline particles, and providing a tracheal tube having a distal tip, a proximal end, a ventilation lumen, and an SP lumen. The tracheal tube is advanced into the patient's trachea until the distal tip of the tracheal tub is positioned above the patient's carina at the separation of the main bronchus into a left bronchus and a right bronchus. A cuff adjacent the distal tip of the tracheal tube is then inflated. The cuff is mounted eccentrically on an exterior of the tracheal tube so that the inflated cuff positions a centerline of the SP lumen along a centerline of the trachea. Once such alignment is achieved, SP from the source may be delivered through the SP lumen into the trachea, and the patient may be ventilated with a gas delivered through the ventilation lumen into the trachea. SP are dispersed within the patient's lungs such that the dispersed SP melt in the lungs to lower a core body temperature of the patient, lower the temperature of targeted organs within the patient, and/or provide localized cooling of the lung within the patient.

The methods of the present invention typically further comprise synchronizing delivery of the SP and the ventilation gas to disperse the SP within the ventilation gas as it is released into the trachea. For example, the SP may be dispersed into the breathing gas in synchrony with the patient's breathing cycle. For example, the SP may be dispersed into the breathing gas during inhalation but not during exhalation. Alternatively, the SP may be dispersed into the breathing gas sequentially with either inhalation or exhalation.

In other optional aspects, the methods of the present invention may further comprise delivering a pharmaceutically or biologically active substance to the patient, in the ventilation gas, within the SP, or within both the ventilation gas and the SP. In some instances, different pharmaceutically or biologically active substances could be delivered simultaneously in the ventilation gas and the SP, respectively.

In other aspects of the present invention, the source of SP comprises storing a volume of pre-formed SP in a hopper. Alternatively, providing the source of SP may comprise comminuting an aggregate source of frozen material into the SP. In still other instances, providing the source of SP may comprise freezing a liquid source material into FSP in situ.

In a third aspect of the present invention, a system for delivering SP including both frozen saline particles (FSP) and other solid particles (SP) to a patient comprises a particle delivery tube as described above, a source of SP, a source of ventilation. The systems may further comprise a controller for controlling the delivery the SP from the SP source and optionally for controlling the delivery of ventilation gas from the ventilation gas source to the patient under conditions wherein the SP are dispersed within the patient's lungs such that the are dispersed in the branching bronchi of the lungs, melting in the case of FSP to lower a core body temperature of the patient. In specific instances, the source of ventilation gas may be a conventional ventilator having an independent controller. In those instances, the controller of the present invention will be coupled to sensors which detect when the patient is inhaling and/or exhaling to allow the delivery of SP to be properly timed with patient inhalation and exhalation. In all instances, the controller of the present invention is operatively connected to the source of SP, where the source may be a hopper containing SP, a system for generating and/or delivering SP, or some combination thereof. In other instances, the controller of the present invention can be configured to control both the source of ventilation gas, and the delivery of SP.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

Figure 1:
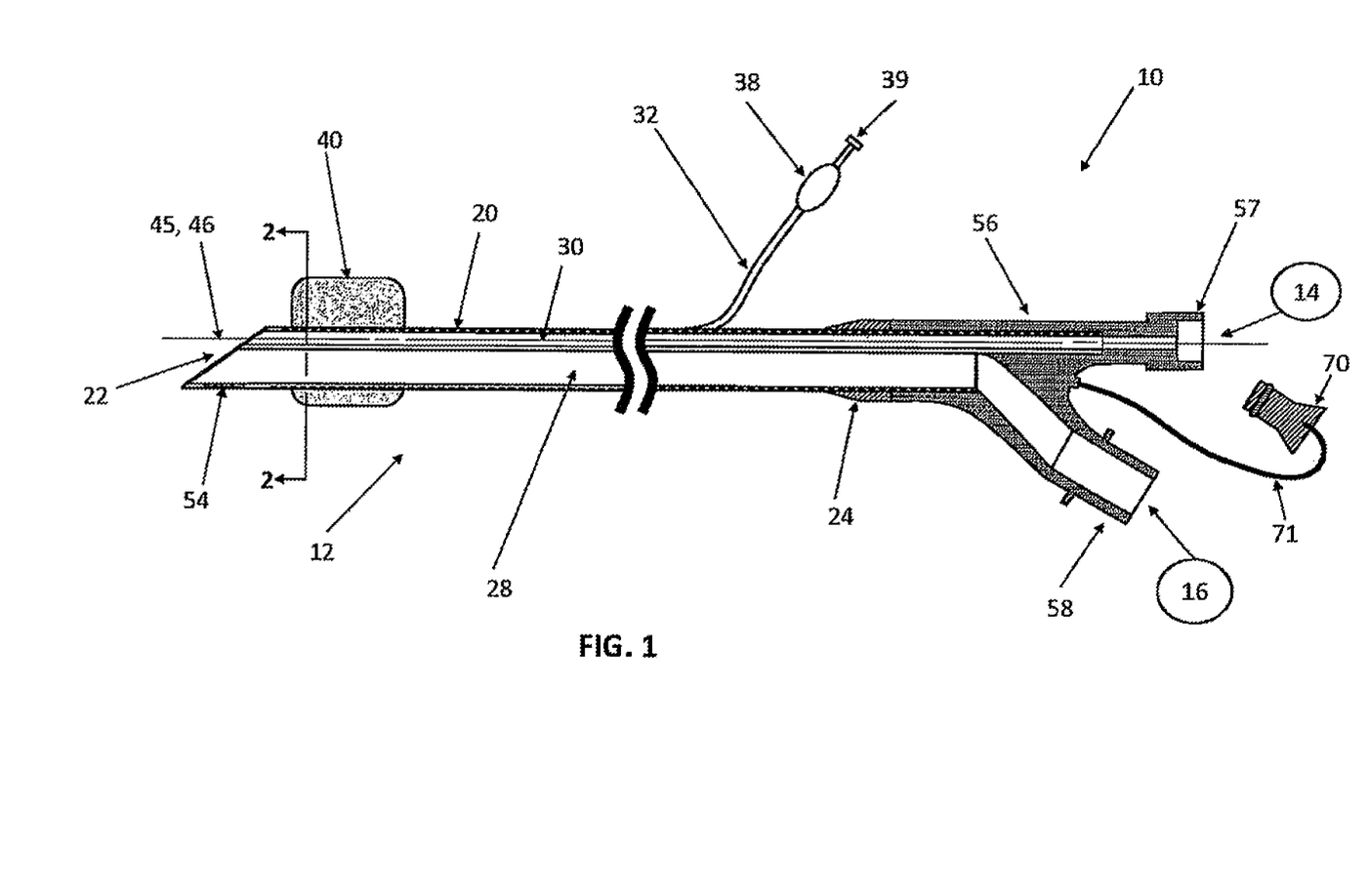
FIG. 1 is a cross-sectional side view of a tracheal tube constructed in accordance with the principles of the present invention shown schematically connected to a solid particle (SP) source and a patient ventilator.

Referring to FIG. 1, a system 10 for delivering solid particles (SP) comprises a tracheal tube 12 connected to an SP source 14 and to a ventilator or other breathing gas source 16. Suitable SP sources (particularly FSP sources) are described in commonly owned co-pending applications US20120167878; U.S. Pat. No. 8,100,123; WO/2017/132609; and WO2018/111778, the full disclosures of which are incorporated herein by reference. Suitable breathing gas ventilators are commercially available. Typically, the SP source 14 comprises FSP, a controller, usually a digital controller, may be provided to control a target temperature (s), rate to target temperature, time at temperature, rewarming rate, both the rate and amount of FSP delivery as well as usually interfacing with the ventilator or ventilation gas to provide for coordination of the FSP delivery and the patient ventilation. Such systems are described in the commonly owned co-pending patent applications previously incorporated herein by reference.

Figure 2:
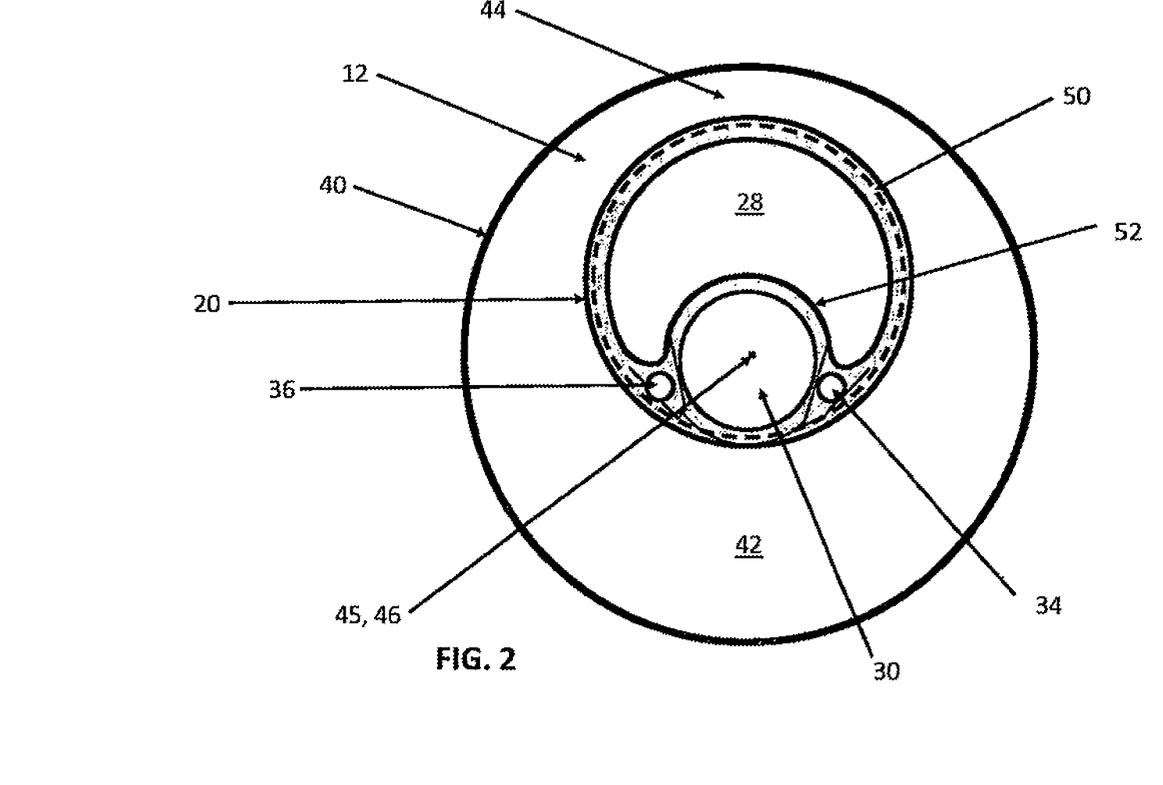
FIG. 2 is a lateral cross-sectional view of the tracheal tube of FIG. 1 taken along line 2-2 in FIG. 1.

The tracheal tube 12 comprises a multi-lumen structure, typically a multi-lumen body 20 which may be in the form of a shaft, tube or other structure suitable for advancement into a patient's trachea, e.g. by advancing the multi-lumen structure through the patient's throat, past the epiglottis and vocal chords, and into the trachea. Alternatively, the multi-lumen structure may be advanced directly into the trachea such as by a tracheotomy. Optionally, as shown in FIG. 2, the multi-lumen body 20 may be reinforced, e.g. with coils, mesh, braid, or other conventional tubular reinforcement elements 50 to enhance hoop strength and provide kink resistance. The reinforcement materials can be metallic (e.g. stainless steel, NiTi (nickel titanium) alloys, etc), polymeric (e.g. liquid crystal polymer), a combination thereof, or other materials. The multi-lumen body 20 can be fabricated and reinforced in a manner similar to the fabrication and reinforcement presently available commercial endotracheal tubes. For example, a core of the multi-lumen body 20 can be extruded and an overlying reinforcement material/structure placed over the extrusion. An outer jacket may then be formed (e.g. by heat shrinking) over the reinforcement elements 50 and the multi-lumen body 20.

Use of a reinforcing material, such as liquid crystal polymer (an inert an unreactive aromatic polymer, such as aramid fiber), enables the construction of a reinforced multi-lumen body that is safe to use in a Magnetic Resonance Imaging machine/environment. Reinforcing the multi-lumen body 20 allows for the use of thinner wall sections which increases the available area for the SP lumen, enabling the incorporation of an SP lumen into the tracheal tube 12 without a significant increase in the outside diameter of the tracheal tube 12 compared to single lumen endotracheal tubes with a similar ventilation area. Alternatively, the tracheal tube 12 may be constructed from two or more separate tubes and configured to provide the SP lumen aligned with the centerline of the trachea T.

The tracheal tube 12 typically has a tapered or beveled distal tip 22 and a hub 56 at its proximal end region. A ventilation lumen 28 and an SP lumen 30 extend in parallel from the proximal hub 56 to the distal tip 22, each terminating in a distal port. An inflation tube 32 is connected to a cuff inflation lumen 34 (FIG. 2) in order to inflate a centering cuff 40. A pilot balloon 38 is attached to or part of the inflation tube 32. The pilot balloon 38 enables the operator to visually determine if the cuff 40 is inflated when the tracheal tube 12 is positioned in the patient. A valve 39 may be attached or part of the pilot balloon 38 or inflation tube 32 to seal the cuff 40 when inflated and allow subsequent deflation. The valve 39 may optionally contain a syringe/inflation device attachment feature, such as a Luer fitting. In place of or in addition to the pilot balloon 38, a pressure transducer may be used. Optionally, an auxiliary lumen 36 (FIG. 2) may be provided for connecting a pressure or temperature sensor, a fiber optic scope, loading radiopaque material, a deflection wire/cable, or the like.

As best seen in FIG. 2, the ventilation lumen 28 typically has a crescent shape with a half-cylindrical inner wall 52 that defines an axial channel or trough within the multi-lumen body 20. The SP lumen 30 is typically nested in the channel defined by the inner wall 52. The cuff inflation lumen 34 and optional auxiliary lumen 36 will typically be disposed where the inner wall 52 intersects with an exterior wall of the multi-lumen body 20.

Figure 3A:
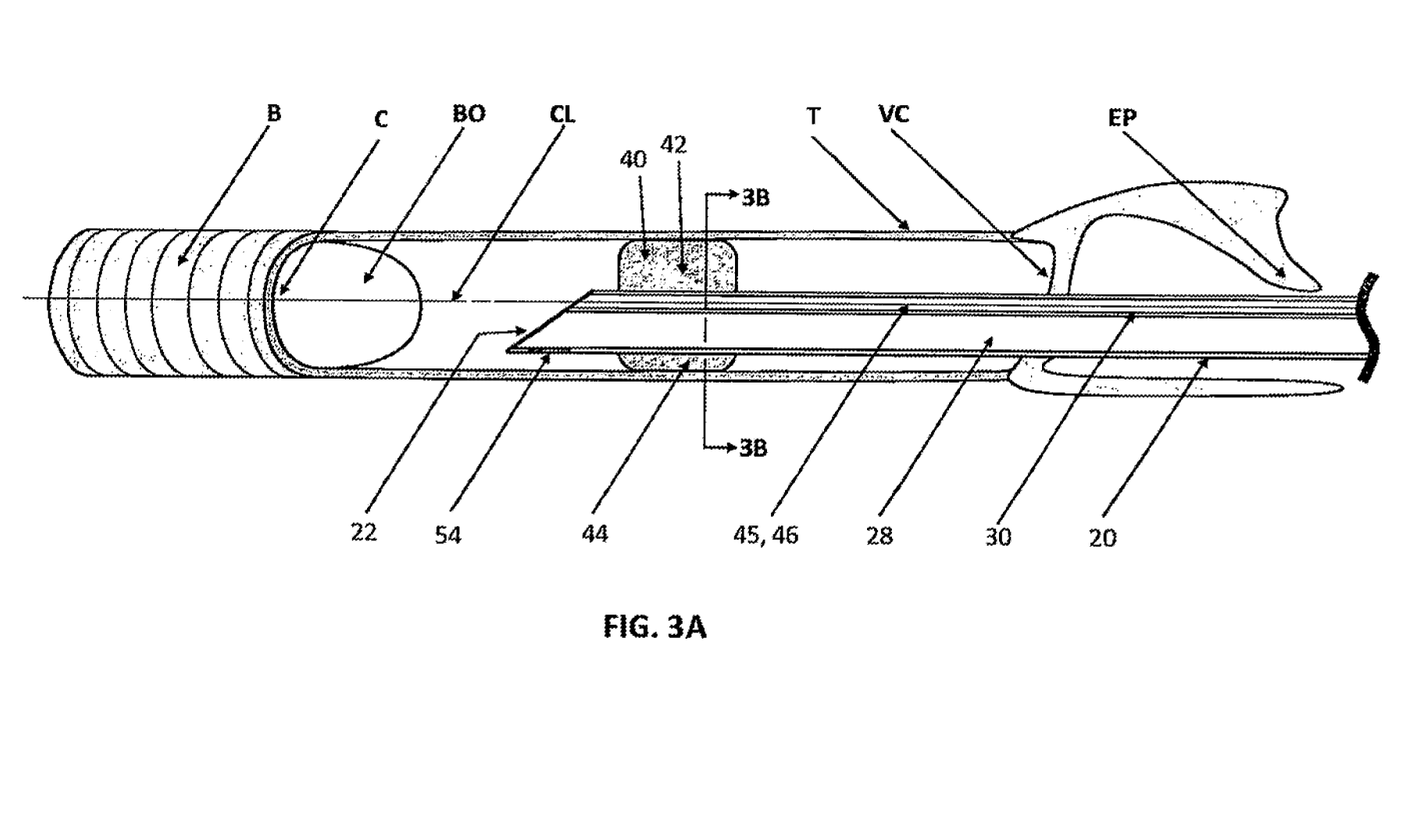
FIG. 3A illustrates the tracheal tube of FIGS. 1 and 2 shown in a patient's main bronchus immediately above a carina which branches into the left bronchus and the right bronchus.
Figure 3B:
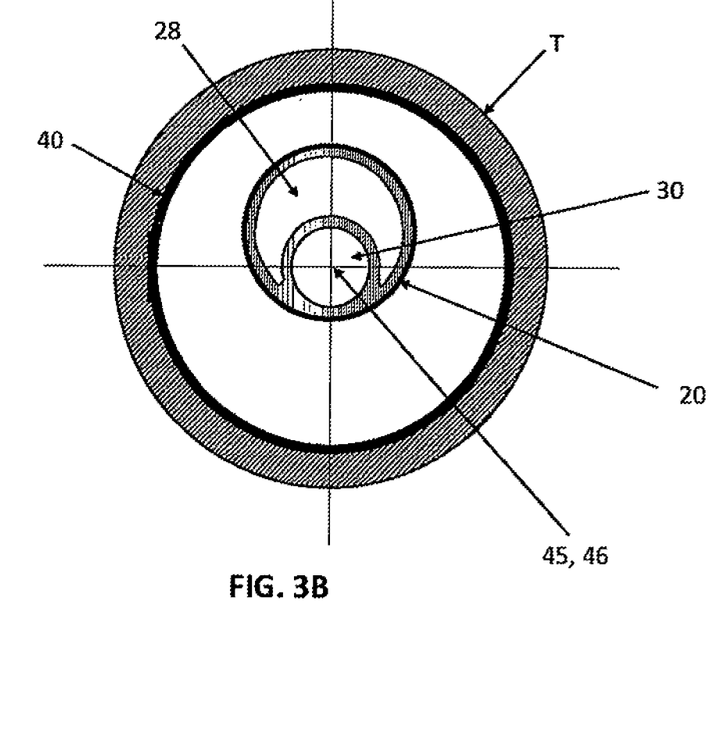
FIG. 3B is a cross-sectional view taken along line 3B-3B of FIG. 3A.

As seen in FIGS. 2, 3A and 3B, the centering cuff 40 is eccentrically mounted on the exterior wall of the distal portion of the multi-lumen body 20 so that a greater portion 42 of the balloon cross-sectional area lies on one side of the multi-lumen body 20 while a lesser portion 44 lies on the other side of the body. The degree of eccentricity of the cuff 40 is typically selected so that a centerline 45 of the cuff 40 coincides with a centerline 46 of the SP lumen 30, as shown in F. As described in more detail below, aligning the centerline 46 of the SP lumen 30 with the centerline of the cuff 40 assures that the SP lumen 30 will be aligned generally at the center of the trachea T in which the tracheal tube 12 is being deployed. While an exact alignment is preferred, an alignment within ±5 mm in the radial direction will usually be sufficient, preferably being within ±2 mm, and more preferably being within ±1 mm. Moreover, while the centerlines of the cuff and the SP lumen be aligned over their entire lengths (i.e. be coincident as shown in FIG. 2), alignment over the distal-most 1 cm will often be sufficient, preferably over the distal-most 2 cm, and more preferably over the distal-most 3 cm.

Referring now to FIGS. 3A and 3B, the tracheal tube 12 is typically delivered to a patient through the patient's mouth so that it passes downwardly through the epiglottis EP, past the vocal chords VC, and into the trachea T. The cuff 40 is inflated to anchor the tracheal tube 12 with the distal tip 22 lying immediately above the patient's carina C. Bronchial openings BO on either side of the carina lead into the patient's bronchus B. Of particular interest, it can be seen that the centerlines 45 and 46 of both the cuff 40 and the SP lumen 30 are aligned (coincident) with the centerline CL of the trachea T.

Optionally, the tracheal tube 12 may be delivered to a patient through the patient's nose so that it passes downwardly through the nasal cavities, past the vocal chords VC, and into the trachea T.

Referring again to FIG. 1, a strain relief sleeve 24 or other structure is positioned at the transition between a proximal region of the tracheal tube 12 which is connected to a hub 56. The hub 56 includes both an SP port 57 and a ventilation port 58. In preferred examples, the SP port 57 is axially aligned (collinear) with the SP lumen 30 in the tracheal tube 12. Such a collinear design reduces the amount of SP that may be lost within the SP port 57 and the SP lumen 30 as the SP are introduced from the SP source 14. The ventilation port 58 is usually connected to the ventilation lumen 28 at an angle since the delivery of gases from the hub 56 into the ventilation lumen 28 is less sensitive to a change of direction.

The SP port 57 will typically be provided with a quick connect that may also be used to connect to the SP source 14 as well as allow access for introduction of a bronchoscope or other catheter-based tools that may or may not benefit from the ability to continuously ventilate during deployment or from the degree of thermal isolation from the body that the SP lumen 30 provides. The ventilation port 58 will typically be 15 mm in diameter with an optional swivel connector to connect to a ventilator or other breathing gas source 16 as well as accept a suction catheter (which could also be deployed through the SP lumen 30 if suction is desired). The hub 56 can be connected to the tracheal tube 12 in a detachable manner, for example using one or more slip fittings, compression fittings, etc. This allows for the hub 56 to be removed from the tracheal tube 12 to allow the user to shorten the length of the tracheal tube 12 and then reconnect the hub 56 to the tracheal tube 12 for use. An SP lumen plug 70 will typically be provided to seal off the proximal end of the SP lumen port 57 to eliminate gas escaping from the patient when the SP lumen port 57 is not connected to the SP source. The SP lumen plug 70 will typically be connected to the hub 56 with a tether 71.

Figure 4:
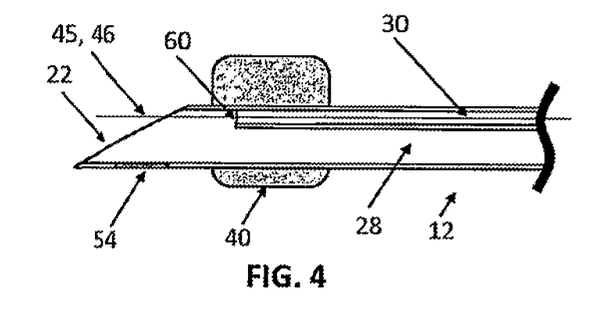
FIGS. 4-10 illustrate alternative constructions of the distal tip region of the tracheal tube of FIGS. 1, 2, 3A, and 3B.

Referring now to FIGS. 4-10, the distal region of the tracheal tube 12 may have any one of a variety of specific constructions to achieve different objectives. While many of these features are illustrated individually in these figures, it will be appreciated that they can also be combined in different embodiments. As shown in FIG. 4, the SP lumen 30 has a distal termination or port 60 located a short distance proximally the open distal tip 22 of the tracheal tube 12, typically by a distance in the range from 5 mm to 50 mm. Such a recess allows the trachea T to be partially shielded from direct impact by SP and mixes the SP with the ventilation gas within the delivery tube as the SP exit the tracheal tube 12, thus reducing the risk of injury to the tracheal wall.

Figure 5:
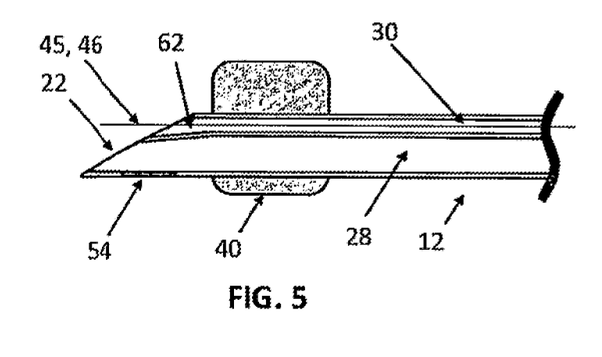

As shown in FIG. 5, a distal region 62 of the SP lumen 30 is flared to increase in cross-sectional area in the distal direction. The increase in cross-sectional area is typically in a range from 2% to 300%, and the flaring occurs over a distance in a range from 5 mm to 50 mm. This flaring changes the release profile of the SP as they exit the SP lumen 30, for example increasing a dispersion area and/or reducing the density of the SP as they are released from the tracheal tube 12 when compared to a non-flared configuration. This dispersion decreases the bulk density of the SP, lessens the impact of the SP on the trachea T, the carina C, bronchus B, and mixes the SP with the ventilation gas more proximally than with a non-flared configuration.

Figure 6:
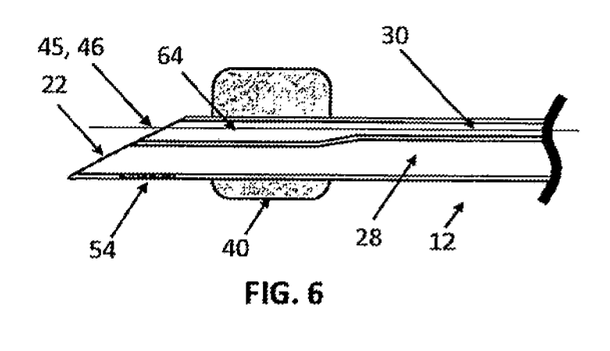

As shown in FIG. 6, a longer flared region 64 at the distal end of the SP lumen 32 will locally reduce the release velocity of the SP before the SP exits the tracheal tube 12. The increase in cross-sectional area is typically in a range from 2% to 300%, and the flaring occurs over a distance in a range from 2 mm to 200 mm. Such a reduction in velocity reduces potential injury to tissue by decreasing the energy of the SP as they impact the wall of the trachea T, carina C, and bronchus B.

Each of the tip designs just described can lessen the local velocity of the SP as they exit the tracheal tube 12. This enables a relatively higher SP velocity to be maintained within the SP lumen 30 in other regions of the tracheal tube 12, and any additional tubing or interconnections going back to the SP source 14 in order to minimize clogging of the tubes, decrease transit duration, and decrease warming of the SP, particularly FSP. Thus, providing flaring and other features as described in FIGS. 4-6 allows much higher velocities to be utilized within the SP transit while reducing the exit velocities to a level which minimizes trauma to the tissue of the trachea T, carina C, and bronchus B. This can be especially desirable when the SP particles are relatively large and/or heavy. In addition, these tip designs also allow for tailoring the distribution of the SP delivery. For example, when delivering a pharmaceutically or biologically active substance to the patient, it may be desirable to have the pharmaceutically or biologically active substance deposited in the upper airways. In this case, a decreased exit velocity or a wider distribution or decreased bulk density of the SP as it exits the tracheal tube 12 would enable improved distribution in the upper airways.

Figure 7:
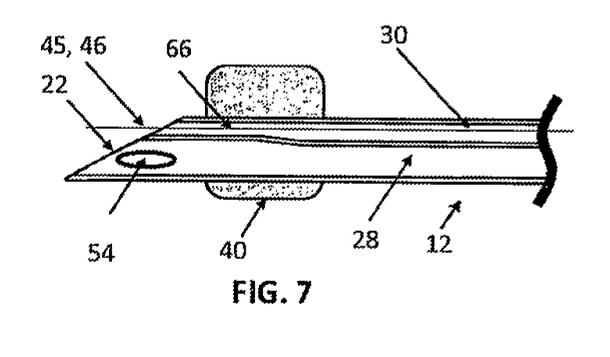

Referring now to FIG. 7, in other instances, the distal cross section of the SP lumen 30 can be narrowed to act as a nozzle in releasing the SP. This tip design will increase the local velocity of the SP as it exits the tracheal tube 12 enabling tailored SP distribution. For example, when it is desired to deposit the SP in the distal airways or when using SP that has a relatively light or very small particle size, increasing the exit velocity can improve the ability of the SP to reach the distal airways. Optionally, one or more Murphy eyes 54 may also be provided at the distal tip of the ventilation lumen 28, as shown in FIG. 7. The use of multiple Murphy eyes 54 may be advantageous as the Murphy eyes 54 may be made smaller to enhance kink resistance of the distal tip 22 of the tracheal tube 12.

Figure 8:
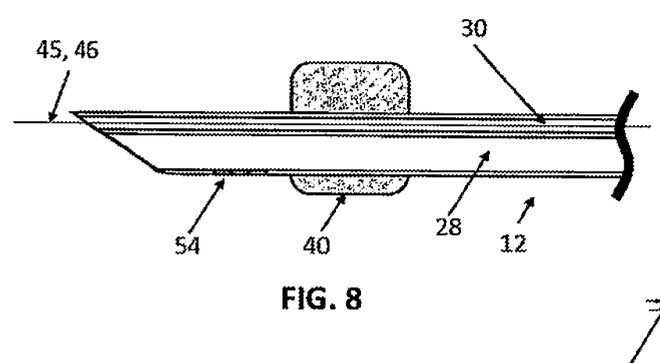

It is generally desirable that the distal end of the SP lumen be located proximally of the distal end of the ventilation lumen 28, in other instances, the distal end of the SP lumen 30 would be disposed distally at the distal end of the ventilation lumen 28 as shown in FIG. 8. Extending the ventilation lumen 28 allows the ventilation gas to begin expanding out into the trachea T (decreasing local velocity) proximally of the exiting SP, in effect creating a relative increase in velocity of the exiting SP compared to the ventilation gas.

Figure 9:
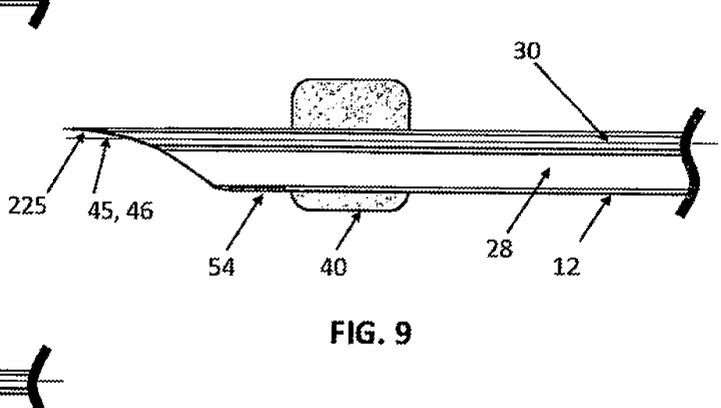
Figure 10:
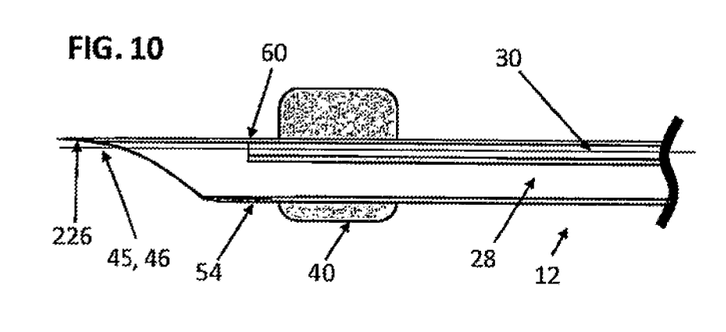

Additionally, as shown in FIGS. 9 and 10, when the exit of the SP lumen 30 is advanced distally relative to the exit of the ventilation lumen 28, a portion of the tracheal tube 12 can be further extended distally to form a protective interface 225, as shown in FIG. 9, or to form a blanket 226, as shown in FIG. 10. This configuration allows increased protection of the tracheal wall from SP impact when the operator places the tracheal tube 12 positioned in the trachea T at an angle relative to the centerline CL of the trachea T. This can happen due to the curvature of the pathway from the mouth or nose to where the cuff 40 is positioned in the trachea.

As can be seen, various tip designs can be used to optimize the distribution and velocity of SP with respect to safety, preferred distribution of the SP within the airways/lungs, as well as to accommodate varying properties of the SP, be it frozen saline particles, pharmaceutically or biologically active substances, or other particles. Combinations of these tip designs may be employed as well as continuing these designs further proximally in the tracheal tube 12. For example, the SP lumen 30 cross-sectional area may be decreased in the proximal section of the tracheal tube 12. All can also be equally applied to delivering into one or more bronchi, with each bifurcation taking the place of the carina.

Figure 11:
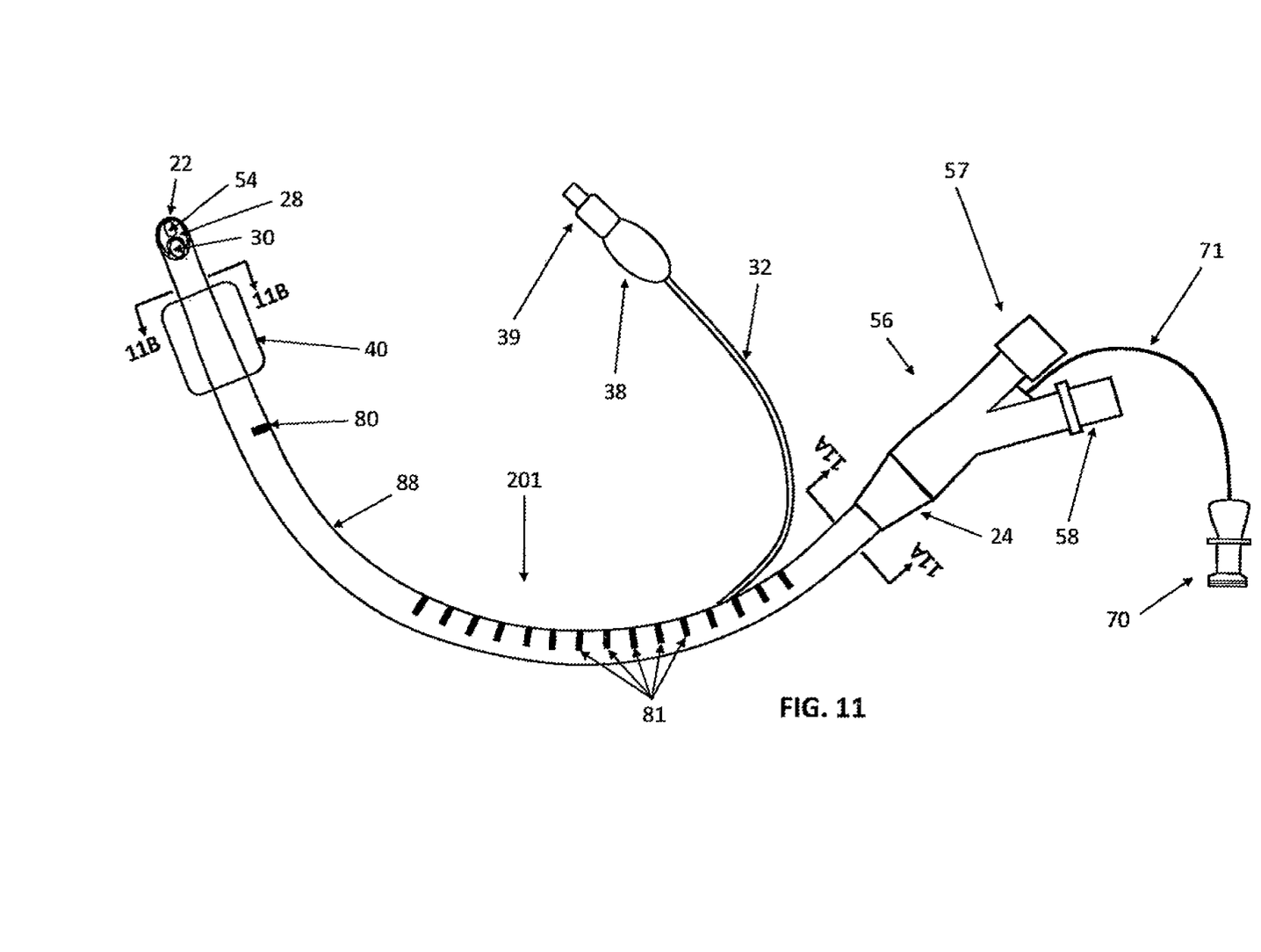
FIG. 11 is a side view of the tracheal tube of FIGS. 1, 2, 3A, 3B shown with a preferred curved shape along at least a portion of its length.

As shown in FIG. 11, in many instances it is desirable to provide a curved multi-lumen body 201 as part of the tracheal tubes of the present invention. The curve may extend from the proximal region of the tracheal tube 12 to the distal tip 22 or the curve may terminate at or proximally of the cuff 40. Various markings may be incorporated on the multi-lumen body 20, such as a glottic depth mark 80, and length marks 81 from the distal tip 22. The previously described Murphy eye 54 is not shown to simplify the illustration.

The tracheal tube 12 ventilation lumen 28 and the SP lumen 30 may rotated or twisted relative to each other along the length of the tracheal tube 12, typically being twisted approximately one-quarter turn (90°) to orient a face of the beveled distal tip 22 in a direction perpendicular to the plane of the curve of the tracheal tube 12 (i.e. facing upwardly from the image plane of FIG. 11) while allowing a plane of the hub 56 (defined by Y-shaped structure of the hub) to remain aligned with the plane of the curve. By "approximately 90°", it is meant that the twist will be within a range from 80° to 100°, usually from 85° to 95°.

Figure 11A:
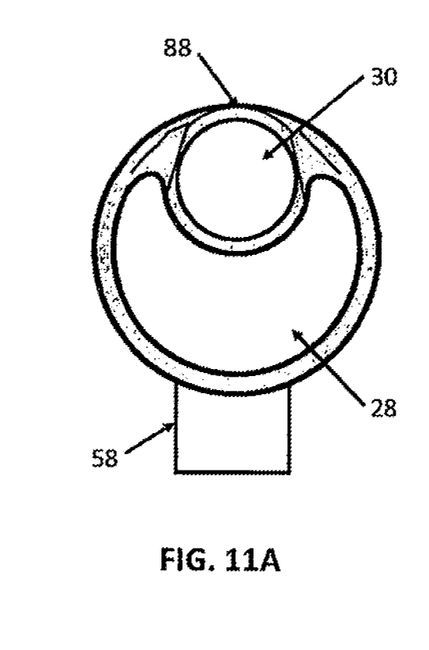
FIG. 11A is a cross-sectional view taken along line 11A-11A of FIG. 11.
Figure 11B:
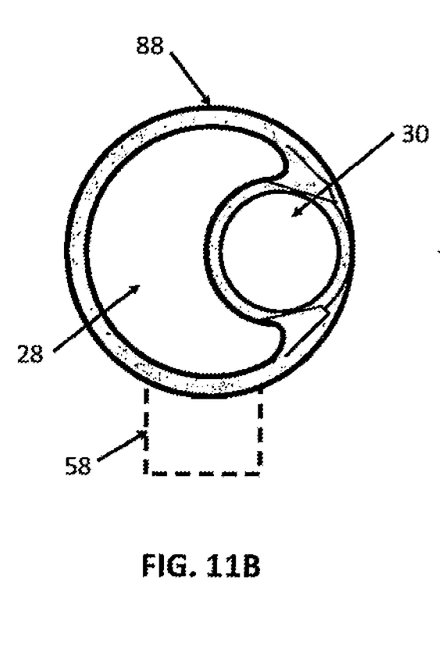
FIG. 11B is a cross-sectional view taken along line 11B-11B of FIG. 11.
Figure 11C:
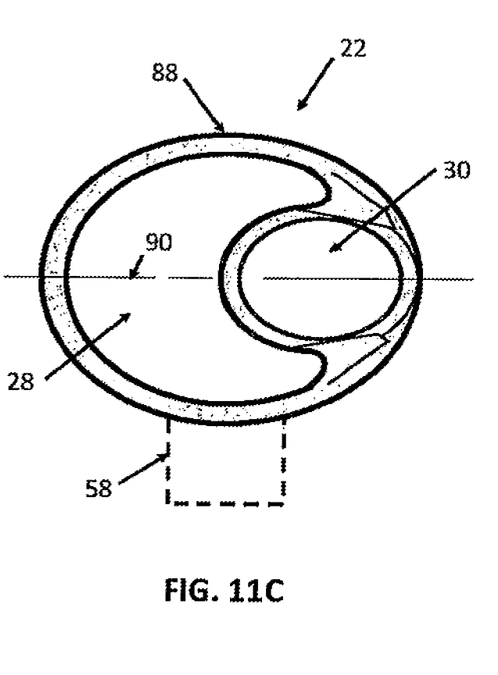
FIG. 11C is a detailed view of a distal face of a beveled distal end of a tracheal tube constructed in accordance with the principles of the present invention.

Referring now to FIGS. 11A-11C as well as FIG. 11, the SP lumen 30 may be positioned along an inside wall 88 of the curved tracheal tube 12 at a proximal end of the tube adjacent to the hub 56, as shown in FIG. 11A. The SP lumen 28 and the ventilation lumen 30 are then twisted one-quarter turn (90°) along the length of the tracheal tube 12 so that SP lumen 30 moves to a side wall of the curved tracheal tube as it approaches the distal end thereof, as shown in FIG. 11B. In this way, the area of the SP lumen will be maximized as a centerline of the SP lumen is aligned with a major axis 90 of the elliptically shaped face of the of the beveled distal tip 22 while preserving the desired bevel orientation facing left when viewed down the tracheal tube 12 from the hub 56 end with the curve pointing up and also for packaging of the tracheal tube 12, as shown in FIG. 11A.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method for delivering solid particles (SP) to a patient's lungs, said method comprising:

providing a source of SP;
   providing a tracheal tube having a distal tip, a proximal region, a ventilation lumen, and a SP lumen;
   advancing the tracheal tube down the patient's trachea until the distal tip is positioned above a carina that separates into a left and a right bronchus;
   inflating a cuff adjacent the distal tip of the tracheal tube, wherein the cuff is eccentrically mounted on an exterior of the tracheal tube so that the inflated cuff positions a centerline of the SP lumen along a centerline of the trachea cuff at a distal face of the tracheal tube;
   delivering SP from the source through the SP lumen into the trachea; and
   delivering a ventilation gas through the ventilation lumen into the trachea; wherein the SP are dispersed into the patient's lungs.

2. A method as in claim 1, further comprising synchronizing delivery of the SP and delivery of the ventilation gas to disperse the SP within the ventilation gas.

3. A method as in claim 2, wherein the SP are dispersed into the ventilation gas in synchrony with the patient's breathing cycle.

4. A method as in claim 3, wherein the SP are dispersed into the breathing gas during inhalation but not during exhalation.

5. A method as in claim 4, wherein the SP are dispersed into the breathing gas sequentially with either inhalation or exhalation.

6. A method as in claim 1, wherein the SP comprise frozen particles.

7. A method as in claim 6, wherein said providing the source of frozen particles comprises storing a volume of preformed frozen particles in a hopper.

8. A method as in claim 6, wherein said providing the source of frozen particles comprises comminuting an aggregate source of frozen material.

9. A method as in claim 6, wherein said providing the source of frozen particles comprises freezing a liquid source material.

10. A method as in claim 1, wherein the SP comprise a pharmaceutically or biologically active substance.

11. A method as in claim 1, further comprising introducing a bronchoscope through a lumen in the tracheal tube and performing bronchoscopy.

12. A method as in claim 11, wherein the bronchoscope is introduced through the SP lumen in the tracheal tube.

13. A method as in claim 1, wherein the tracheal tube comprises a multi-lumen body having the ventilation lumen and the SP lumen formed therein.

14. A method as in claim 13, wherein the ventilation lumen has a crescent-shaped cross section with a half-cylindrical inner wall.

15. A method as in claim 14, wherein the SP lumen is nested in a channel formed in the half-cylindrical inner wall of the ventilation lumen.

\* \* \* \* \*